(12) United States Patent
Gallagher

(10) Patent No.: US 6,907,785 B1
(45) Date of Patent: Jun. 21, 2005

(54) DIAGNOSTIC SENSOR

(75) Inventor: John G Gallagher, North Yorkshire (GB)

(73) Assignee: Hydramotion Limited, Malton (GB)

( * ) Notice: Subject to any disclaimer, the term of this patent is extended or adjusted under 35 U.S.C. 154(b) by 0 days.

(21) Appl. No.: 09/744,818

(22) PCT Filed: Jul. 6, 1999

(86) PCT No.: PCT/GB99/02160

§ 371 (c)(1),
(2), (4) Date: Jan. 30, 2001

(87) PCT Pub. No.: WO00/04370

PCT Pub. Date: Jan. 27, 2000

(30) Foreign Application Priority Data

Jul. 15, 1998  (GB) .............................................. 9815232

(51) Int. Cl.$^7$ ........................... G01N 29/00; G01P 15/08
(52) U.S. Cl. ..................... 73/579; 73/54.27; 73/514.29; 73/862.59
(58) Field of Search ...................... 73/579, 1.83, 32 A, 73/54.02, 54.25, DIG. 1, 514.29, 862.41, 862.59, 54.27; 310/321

(56) References Cited

U.S. PATENT DOCUMENTS

| | | | |
|---|---|---|---|
| 4,095,474 A | | 6/1978 | Hancock |
| 4,299,122 A | | 11/1981 | Ueda |
| 4,644,796 A | * | 2/1987 | Ward .............................. 73/702 |
| 4,922,745 A | * | 5/1990 | Rudkin et al. ............... 73/32 A |
| 5,201,215 A | * | 4/1993 | Granstaff et al. ........... 73/54.41 |
| 5,804,698 A | * | 9/1998 | Belonenko et al. ........... 73/1.83 |
| 5,831,178 A | * | 11/1998 | Yoshimura et al. ..... 73/861.357 |
| 5,889,351 A | * | 3/1999 | Okumura et al. ............ 310/321 |
| 6,389,877 B1 | * | 5/2002 | Takeuchi et al. ............ 73/19.03 |
| 6,457,361 B1 | * | 10/2002 | Takeuchi et al. ............... 73/580 |
| 6,484,578 B2 | * | 11/2002 | Woodruff et al. ......... 73/514.29 |
| 6,516,651 B1 | * | 2/2003 | Geen ............................ 73/1.16 |

FOREIGN PATENT DOCUMENTS

| | | |
|---|---|---|
| EP | 0 087 612 | 9/1983 |
| EP | 0 129 753 | 1/1985 |
| EP | 0 282 251 | 9/1988 |
| WO | WO 91 17423 | 11/1991 |

OTHER PUBLICATIONS

Langdon, "Resonator sensors—a review" Journal of Physics E. Scientific Instruments, vol. 18, 1985, pp. 103–115., IOP Publishing, Bristol.

* cited by examiner

*Primary Examiner*—Hezron Williams
*Assistant Examiner*—Jacques M. Saint-Surin
(74) *Attorney, Agent, or Firm*—Nixon & Vanderhye PC

(57) ABSTRACT

A sensor of force or viscosity or other attributes of a fluid comprises a mechanical resonator (10) including an element (11; 18; 123) of which the stiffness at least partially determines a modal shape of the resonance of the resonator and means (21–23) for measuring a variation of a measure of the resonance as the stiffness of said element changes. The resonator (10) may comprise two beams (10a, 10b; 120, 121) connected at or near one end by a yoke (12; 122) which provides a clamped condition of the resonator at said one end and connected at or near another end by said element.

5 Claims, 5 Drawing Sheets

DIAGNOSTIC SENSOR

This invention is concerned with the use of a vibrating resonant structure for the measurement of physical and chemical properties of fluids and solids.

It is known to measure an attribute such as the density or viscosity of a medium, whether solid or fluid, by measuring some characteristic or parameter of vibration of a vibratile structure. Some examples which illustrate the general state of the art are shown in U.S. Pat. Nos. 5,023,560, 5,363,691 and 5,670,709.

The present invention is based on measuring vibration of amplitude, phase or frequency of a mechanical resonator as a result of a change in modal shape of a resonant system, caused for example by a change in stiffness of a beam element which form part of or is coupled to the resonator.

DETAILED DESCRIPTION

Various embodiments are described by way of example to illustrate the principles employed in the invention.

Figure 1:
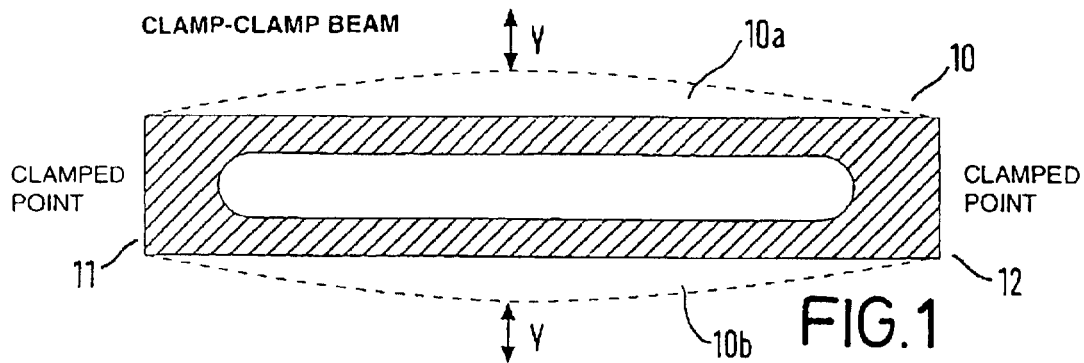
FIGS. 1 and 2 illustrate beam resonators various resonant systems.

FIG. 1 illustrates a beam resonator 10 comprising two substantially parallel beams 10a and 10b which are rigidly connected at their extremities. The connections of the beams at their extremities are substantial and yokes 11 and 12 formed at the extremities have a high stiffness. The beams are therefore referred to, in the terminology of modal beam analysis, as 'clamped'. The vibration of the beams is denoted by the arrows Y.

Figure 2:
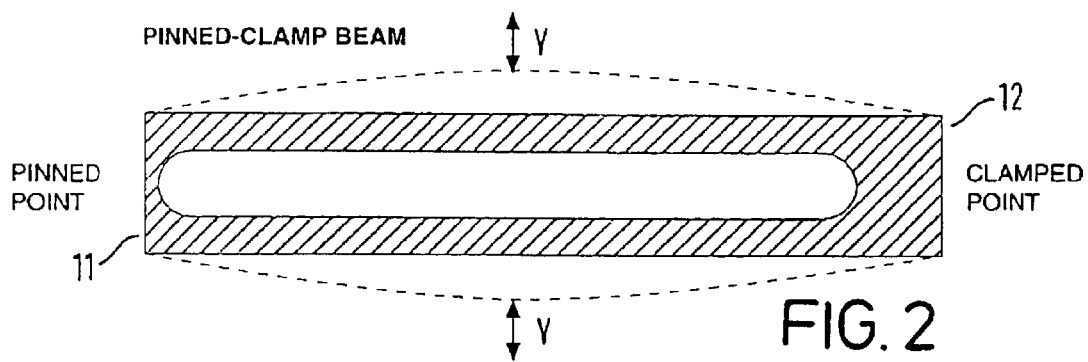

Such a resonator, referred to herein as 'clamp-clamp', will resonate at a first mode natural frequency given by the equation:

$$f = 22.3733 \sqrt{(EI/ML^4)} \qquad (1)$$

f=Frequency
E=Young Modulus
I=Mass Moment of Inertia
M=Mass/Unit Length
L=Beam Length If the connecting yoke 11 at one end of the resonator 10 is substantially weakened the beams can no longer be considered clamped, as they are allowed a degree of rotation about their connection point, in the terminology of modal beam analysis the yoke is then approaching the 'pinned' condition. This condition is shown in FIG. 2, and the 'clamp-pinned' system will now resonate at a natural frequency given by the equation:

$$f = 15.4182 \sqrt{(EI/ML^4)} \qquad (2)$$

From equations (1) and (2) it can be seen that the transition from fully clamped to fully pinned results in an approximately 30% change in frequency. If the yoke connection is lost the beams are referred to as 'free', and the clamped-free system now resonates at a natural frequency given by the equation:

$$f = 3.516 \sqrt{(EI/ML^4)} \qquad (3)$$

From equations (2) and (3) it can be seen that the transition from fully pinned to fully free results in an approximately 77% change in frequency.

Figure 3:
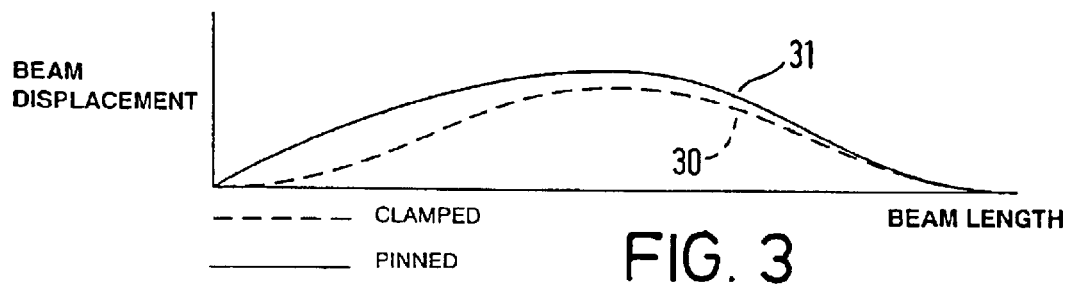
FIGS. 3 and 4 illustrate various resonant characteristics.
Figure 4:
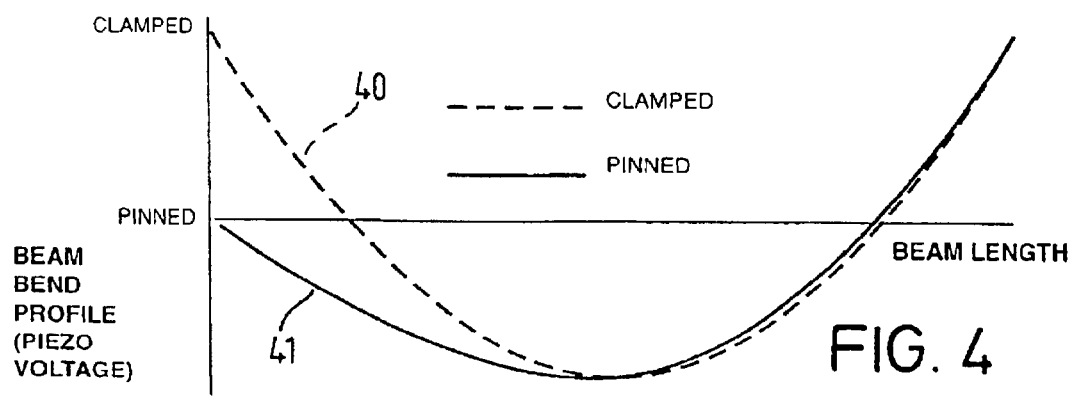

In addition to a change in frequency, the modal shape of the clamp-clamp system differs significantly to that of the clamp-pinned arrangement. A generalised view of the displacement of the beam in clamped and pinned mode is shown in FIG. 3. The curve 30 illustrates the variation in maximum displacement of the beam over its length when the yokes 11 and 12 are 'clamped'. The curve 31 illustrates the corresponding displacement when the yoke 11 is 'pinned'. FIG. 4 shows the variation of local beam bending with respect to position along the beam for the clamp-clamp state (curve 40) and the clamp-pinned state (curve 41). There are further modal changes as the clamp-pinned condition progresses to clamped-free.

A sensor, such as a piezoelectric device, responding to localised beam flexure would exhibit a signal response with position along the length of the beam in a manner similar to the profiles shown in FIG. 4. As well as a voltage amplitude variation with length there can also be observed a polarity change, or phase change, of the vibration signal along the length.

In summary, the transition from a clamp-clamp state to a clamp-pinned state, or from a clamp-pinned state to a clamp-free state results in changes in frequency, amplitude and phase of vibration relative to position on beam. It also follows that a change from clamp-clamp to clamp-free will obviously have a similar result. The measurement of change of these parameters in response to an event influencing the modal classification of the resonator (e.g. clamp-clamp to clamp-pinned, clamp-pinned to clamp-free) forms the basis of this invention.

In applications where there is depletion of a substance or build-up of material, such as corrosion or scaling, the actual substrate may form a stiffening member on the beam yoke and thus contribute to the status of the yoke as clamped or pinned.

Figure 5:
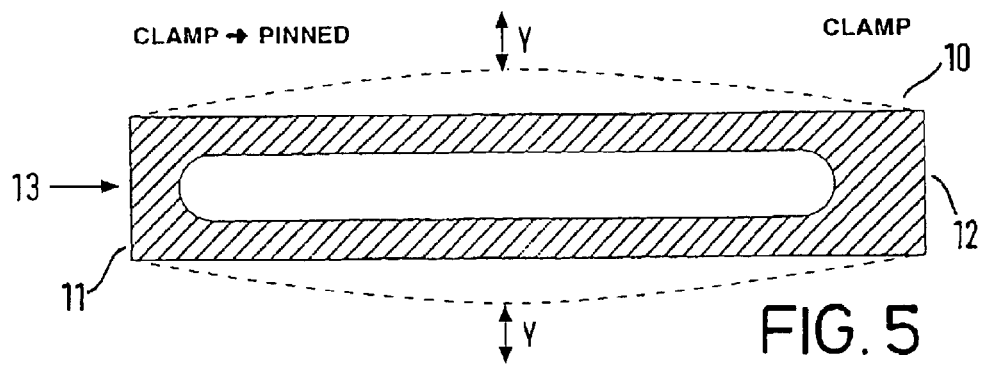
FIGS. 5 to 8 illustrate various beam resonators.

FIG. 5 shows a simple embodiment of a dual beam system, similar to that shown in FIG. 1. Depletion of material at the connection of the beams forming yoke 11 produces a thinner, less substantial connection as shown at 13 in FIG. 5 and can produce a change to a pinned state at this end of the resonator. However in general such a system would require significant depletion of material to manifest a modal change.

Figure 6:
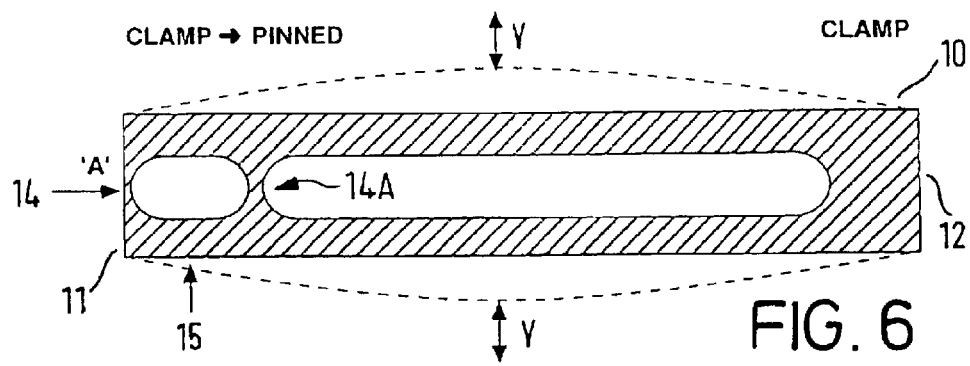
Figure 7:
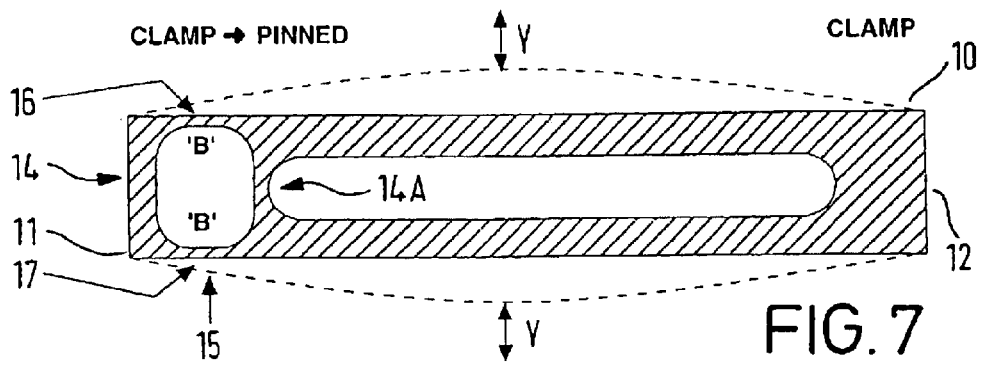

Improvements on this basic system are shown in FIG. 6 and FIG. 7; in both these cases the simple connection yoke 11 is replaced by a box section 15. The section achieves its stiffness from the spatially separated members 14 and 14a, and a small reduction of thickness of a part of either member 14, 14a will manifest a substantial change in rigidity—thus altering the stiffness of the section.

FIG. 6 particularly shows a system where in the rigidity of the box section is modulated by the longitudinal stiffness of the member 14. FIG. 7 shows the segments 16 and 17 between the members 14 and 14a; they will significantly influence the rigidity of section 15 if their flexural or longitudinal stiffness is altered.

Figure 8:
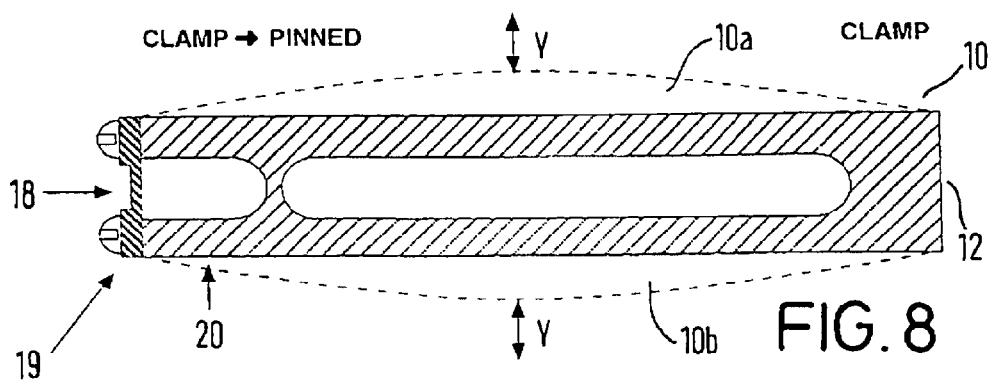

FIG. 8 shows a refinement of the system in FIG. 6 and allows for a 'bolt-on' section stiffener 18 to be used to join the beams at the end in place of member 14. The stiffener 18 is secured by bolts 19 to each of the beams 10a and 10b, This forms a convenient means of selecting the material, shape and size of a section member to suit a particular application.

Figure 9A:
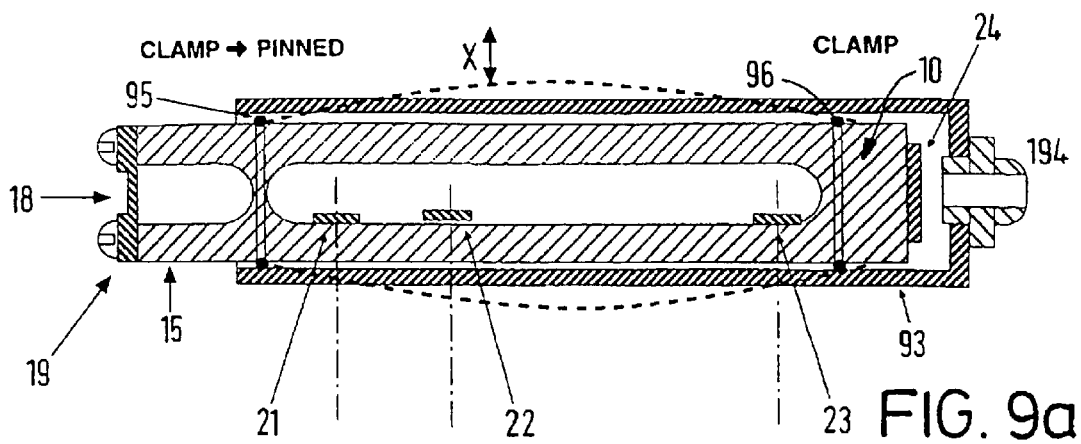
FIG. 9 illustrates a particular embodiment of the invention (FIG. 9A) and characteristics of its resonant modes (FIG. 9B).

FIG. 9A illustrates a specific embodiment based on the system shown in FIG. 8, although in principle any of the systems previously described could be used. Piezoelectric transducers are strategically placed to indicate the amplitude and phase of the flexure of the beam at a specific location. The signal from each transducer relates directly to the modal pattern formed by the clamp or pinned condition of the yoke. Lateral vibration of the beam structure is shown by the arrows Y.

In the system shown in FIG. 9A, piezoelectric transducers 21, 22 and 23 are disposed at different locations along the inner surface of the lower beam 10b in order to obtain a measure, represented by the relevant piezo output voltage, of the displacement of the beam at those locations when the system is in a resonant vibratory mode induced by a drive piezoelectric transducer 24 disposed (in this example) at the clamped end of the resonant beam system. In this system the transducer 23 acts as a reference, because it is located close to a node and the displacement of the adjacent part of the resonator is minimal. The drive transducer 24 may have a regenerative feedback connection (known per se in the art) from one or more of the sensing transducers 21, 22 or 23. Electromagnetic drive and sensing transducers may be used in place of piezoelectric transducers. Other forms of transducer, such as capacitative, optical or acoustic transducers may be used as appropriate.

Figure 9B:
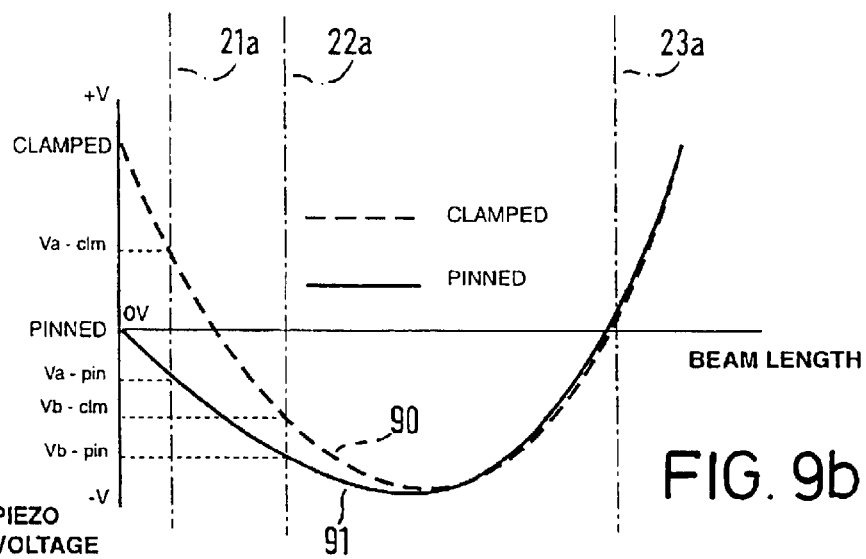

FIG. 9B is a graph of piezo voltage against distance measured along the beam, the curves 90 and 91 being for the clamped and pinned condition respective at the end 11. The particular piezo voltages are given by the intersections of the projection lines 21, 22a and 23a (through respective transducers 21, 22 and 23) with the curves 90 and 91.

The embodiment shown in FIG. 9 includes an enclosure 93 for the sensor, the enclosure comprising a tube which has a gland 94 for wires to pass to the transducers through a closed end of the tube. O-ring seals 95 and 96 are disposed between the beam structure 10 and the tube near the ends of the tube, from the open end of which the box section 15 protrudes.

Figure 10:
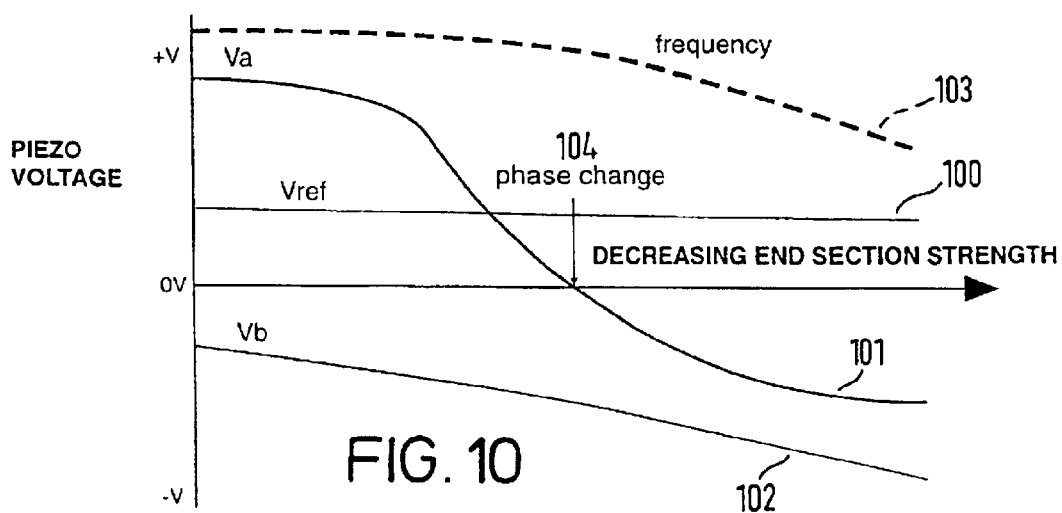
FIG. 10 illustrates a resonant characteristic.

FIG. 10 illustrates the variation of the piezoelectric voltages $V_a$ and $V_b$, from the sensors 21 and 22 (curves 101 and 102) and the frequency of resonance (curve 103), as a function of the decreasing stiffness of the section stiffener 18. Curve 101 exhibits a phase change (shown at 104). The curve 100 shows the substantially constant piezo voltage $V_{ref}$ obtained from the transducer 23. It follows that the progress of any physical, chemical, or biological effect leading to the depletion or build-up of the sacrificial section stiffener material can be monitored by measuring the modulation or variation of these piezoelectric sensor signals over time. As an example, a section stiffener made from iron will have its thickness, and hence its stiffness depleted, in a corrosive environment over time and measurement of Va, Vb or frequency will indicate the rate of corrosion. It further follows that selection of other materials in the electrochemical series can exhibit the same corrosion/deposition effects in the appropriate electrolyte or reactive medium.

Signal processing techniques, such as the following, can be employed to enhance the result:

(a) Division of Va by Vb will result in a ratio dependent on section stiffness but independent of amplitude of signals or system damping.

(b) Division of Va or Vb by Vref will result in a ratio dependent on section stiffness but independent of amplitude of signals or system damping.

(c) Measurement of phase of Vb will form a simple method of indicating the point at which a specific section stiffness is reached.

(d) A plurality of piezoelectric sensor mounted alone the beam can be monitored for change of phase to indicate progress of change of section stiffness.

(e) If the resonator is at fill temperature equilibrium with its environment the modal shape will indicate section stiffness independently of temperature.

(f) Frequency signal has some temperature dependency so comparison of modal shape with frequency signal will yield both temperature and section stiffness from a single resonator.

Figure 11:
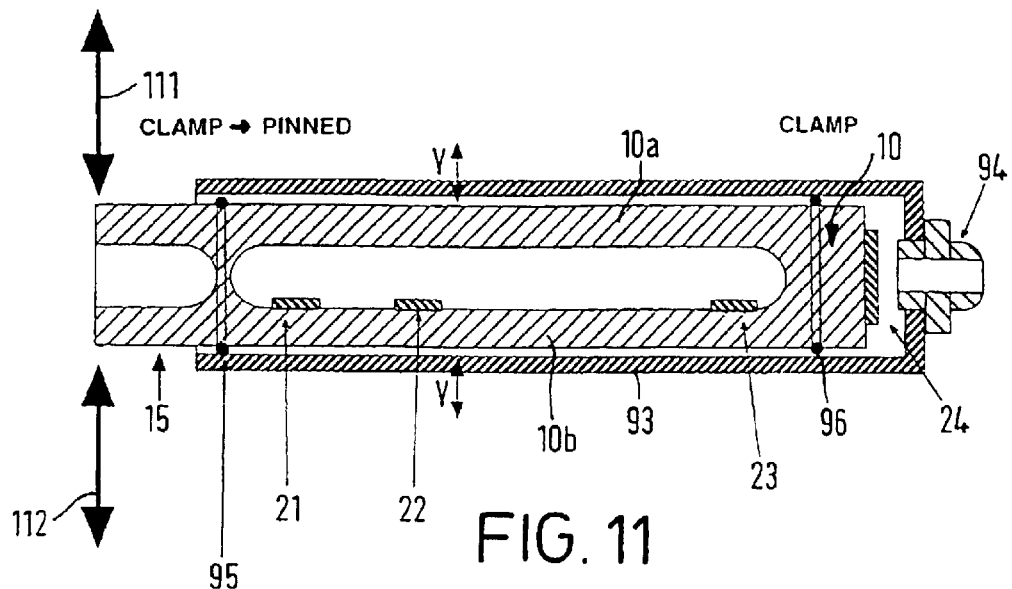
FIG. 11 illustrates another embodiment of the invention.

In general terms the invention can provide a force transducer. With the section stiffener removed as shown in FIG. 11 (which otherwise resembles FIG. 9) the stiffness of the pinned yoke will be altered towards the clamped state by the presence of external forces 111, 112 on the yoke, either in compression or tension. These forces can be mechanical, electrical or magnetic.

The movement of the beams 10a and 10b will create a velocity and therefore a shear action within a fluid. By measuring energy loss, or the quality factor Q, of the signal the viscous shear loss can be determined, and thus the fluid viscosity. Similarly, the damping capacity of any solid connected to the yoke can be determined from the Q of the resonant signal.

The elastic properties of a viscoelastic fluid can be derived from the change in resonant frequency due to the stiffening of the yokes a result of the elastic modulus of the fluid.

Figure 12:
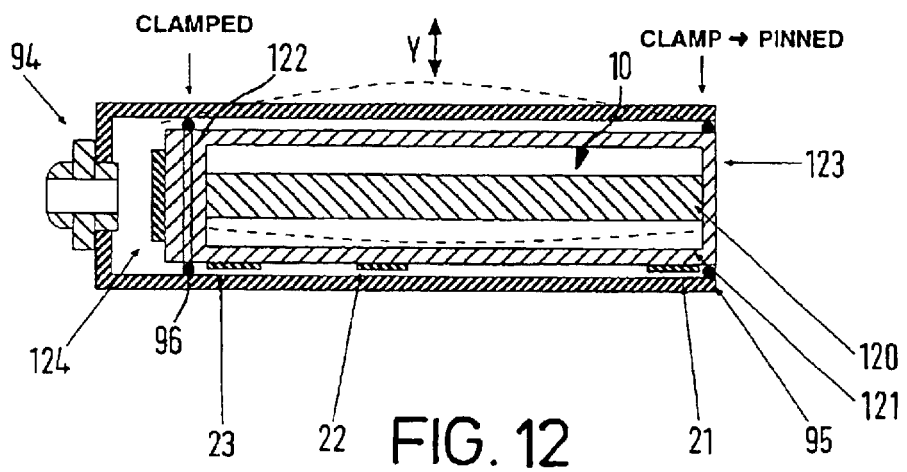
FIG. 12 illustrates another embodiment of the invention.

FIG. 12 illustrates sectionally a different embodiment in which the beam structure 10 comprises an internal cyclindrical beam 120 and an external cylindrical beam 121. The beams are connected by a relatively thick yoke member 122 at a 'clamped' end and by a yoke member 123 at the other end. Reduction of the stiffness of this yoke 123 changes the connection at this end from 'clamped' to 'pinned'.

FIG. 12 includes sensing transducers 21, 22 and 23 disposed on the external beam and a drive transducer 24 disposed on the yoke member 122. The beam structure is enclosed by a tube 93 which has a gland 94 and intermediate O-ring seals 95 and 96.

Figure 13:
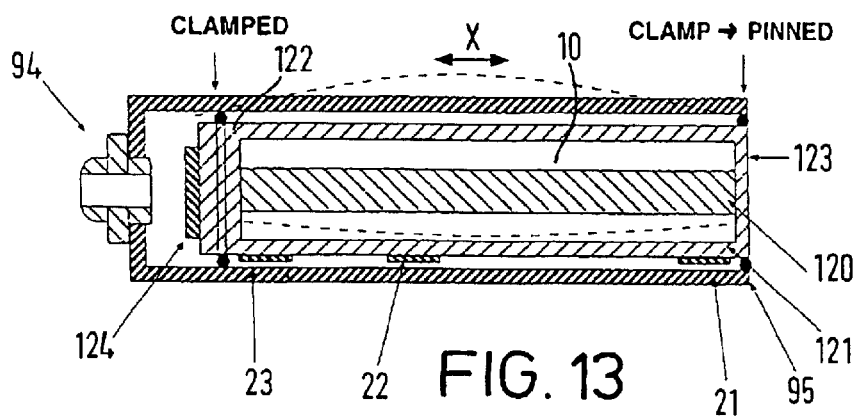
FIG. 13 illustrates the embodiment shown in FIG. 12 but vibrating in a different mode.

FIG. 13 is similar to FIG. 12 but illustrates vibration of the structure in a longitudinal mode (arrow X).

Figure 14A:
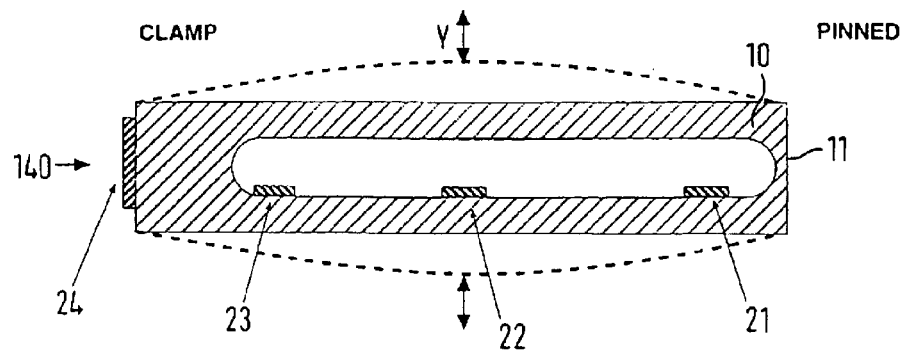
FIGS. 14a and 14b illustrate the change of a resonator from a 'clamped-pinned' state to a 'clamped-free' state.
Figure 14B:
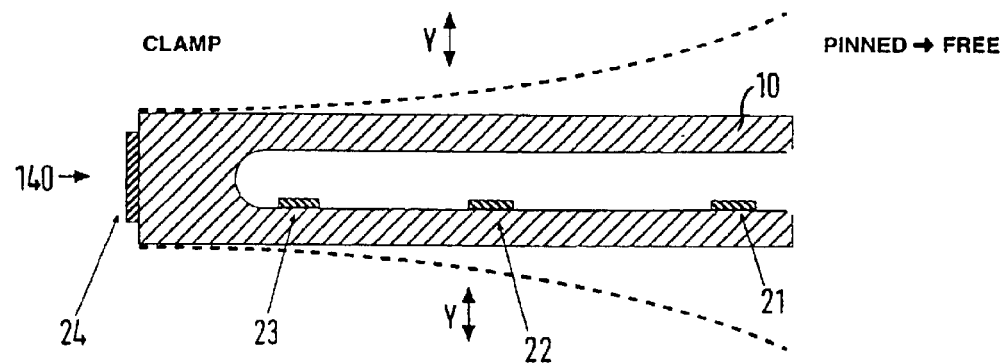

As a further example, FIGS. 14a and 14b shows the degeneration of a clamp-pinned structure 10 shown in FIG. 14a to the clamp-free condition as the member 11 at one end vanishes The structure is clamped at its other end 140.

All the resonators can be operated in harmonic modes above the natural frequency. There are proportional movements in modal/frequency behaviour at higher modes than a fundamental mode.

What is claimed is:

1. A sensor, comprising:

a mechanical resonator comprising two beams, a yoke rigidly connecting said beams at a first location so that said beams are mutually clamped at said first location, and a connecting element connecting the beams at a second location spaced from the first location along the beams, said connecting element having a stiffness that at least partially determines a modal shape of resonant vibration of the beams; and at least one transducer, disposed adjacent one of the beams at a location between said first and second locations, and being disposed to sense a vibrational parameter that indicates a variation of said modal shape.

2. A sensor as set forth in claim 1, wherein said connecting element provides a clamped connection of said beams at said second location, and wherein said at least one transducer senses a variation of said modal shape from a clamped-clamped shape to a clamped-pinned shape.

3. A sensor as set forth in claim 1, wherein said connecting element provides a pinned connection between said beams at said second location, and wherein said at least one transducer senses a variation of the modal shape from a clamped-pinned condition to a clamped-free condition.

4. A sensor, comprising:

a mechanical resonator comprising two parallel beams;

a yoke connecting said beams together at a first discrete location;

a box section connecting said beams together at a second discrete location spaced apart from said first discrete location, said box section including first and second spaced connecting elements which connect the beams together, said connecting elements having stiffnesses that at least partly determine a modal shape of resonant vibration of the resonator; and at least one transducer disposed between the first and second locations to measure a vibrational parameter that indicates variation of said modal shape.

5. A method of sensing, comprising:

deploying a sensor comprising a mechanical resonator comprising two parallel beams and at least two connecting elements which connect the beams together at different, space apart, locations, at least one of said connecting elements having a stiffness which determines a modal shape of resonant vibration of the resonator, and at least one transducer disposed to provide a vibrational parameter which indicates a variation of said modal shape;

exposing one of said connecting elements to an environment which physically alters one of said connecting elements so as to alter its stiffness; and monitoring a change in said modal shape.

* * * * *